US011642299B1

(12) United States Patent
Benchaouir et al.

(10) Patent No.: US 11,642,299 B1
(45) Date of Patent: May 9, 2023

(54) USE OF SCLERITINE AS AGENT FOR PROTECTING CELLS AGAINST TOXIC AGENTS

(71) Applicants: CENTRE SCIENTIFIQUE DE MONACO, Monaco (MC); CORALIOTECH, Monaco (MC)

(72) Inventors: Rachid Benchaouir, Montrouge (FR); Pierre-Olivier Buclez, Elancourt (FR)

(73) Assignees: CENTRE SCIENTIFIQUE DE MONACO, Monaco (MC); CORALIOTECH, Monaco (MC)

( * ) Notice: Subject to any disclaimer, the term of this patent is extended or adjusted under 35 U.S.C. 154(b) by 393 days.

(21) Appl. No.: 16/646,109

(22) PCT Filed: Sep. 11, 2018

(86) PCT No.: PCT/EP2018/074455
§ 371 (c)(1),
(2) Date: Mar. 10, 2020

(87) PCT Pub. No.: WO2019/048703
PCT Pub. Date: Mar. 14, 2019

(30) Foreign Application Priority Data

Sep. 11, 2017 (FR) ...................................... 1758347

(51) Int. Cl.

| | |
|---|---|
| ***A61K 8/64*** | (2006.01) |
| ***A61Q 17/00*** | (2006.01) |
| ***A61K 9/00*** | (2006.01) |
| ***A61Q 17/04*** | (2006.01) |
| ***A61K 38/17*** | (2006.01) |

(52) U.S. Cl.
CPC ................ *A61K 8/64* (2013.01); *A61K 38/17* (2013.01); *A61K 38/1767* (2013.01); *A61Q 17/00* (2013.01); *A61Q 17/04* (2013.01); *A61K 9/0014* (2013.01)

(58) Field of Classification Search
None
See application file for complete search history.

(56) References Cited

U.S. PATENT DOCUMENTS

2016/0136074 A1* 5/2016 Daly ...................... A61Q 19/00 424/59

FOREIGN PATENT DOCUMENTS

CN 1346638 A 5/2002
WO WO-2010078879 A2 * 7/2010 ............ A61K 8/987

OTHER PUBLICATIONS

Debreuil et al., Julien, "Molecular Cloning and Characterization of First Organic Matrix Protein for Sclerites of Red Doral, Corallium rubrum," Journal of Biological Chemistry, vol. 287, No. 23, Jun. 2012, pp. 19367-19376.
Rahman, M. Azizur, "An Overview of the Medical Applications of Marine Skeletal Matrix Proteins," Marine Drugs, vol. 14, No. 9, 167, September 206, pp. 1-9.
International Search Report issued in corresponding International Application No. PCT/EP2018/074455, dated Nov. 26, 2018, pp. 1-8, European Patent Office, Rijswijk, Netherlands.
Written Opinion issued in corresponding International Application No. PCT/EP2018/074455, dated Nov. 26, 2018, pp. 1-5, European Patent Office.

* cited by examiner

*Primary Examiner* — Jennifer A Berrios
(74) *Attorney, Agent, or Firm* — Hauptman Ham, LLP

(57) ABSTRACT

Scleritine is used as a protective agent for cells against toxic agents, in particular chemical or physical agents. One or more embodiments relate to a dermatological and/or cosmetic composition, which protects the skin against toxic agents, characterized in that it comprises Scleritine in at least one excipient or vehicle adapted to a topical application. One or more embodiments concerns the pharmaceutical or cosmetic industry and more specifically the formulation of pharmaceutical or cosmetic compositions intended to protect cells against toxic agents.

14 Claims, 3 Drawing Sheets

Figure 1:
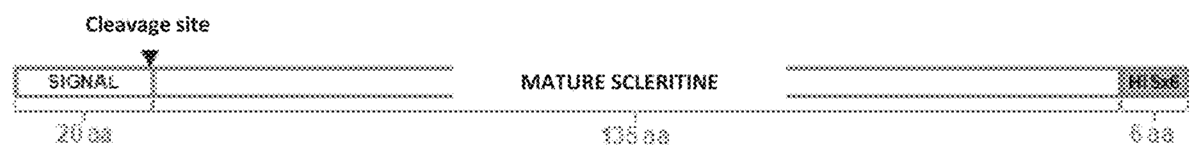

Specification includes a Sequence Listing.

USE OF SCLERITINE AS AGENT FOR PROTECTING CELLS AGAINST TOXIC AGENTS

The present application is a National Phase of International Application Number PCT/EP2018/074455, filed Sep. 11, 2018, which claims priority to French Application No. 1758347, filed Sep. 11, 2017, and both are hereby incorporated by reference in their entirety into the present application.

INCORPORATION BY REFERENCE

The sequence listing provided in the file entitled Sequence_ANG_20201201, which is an ASCII text file that was created on Dec. 1, 2020, and which comprises 4665 bytes, is hereby incorporated by reference in its entirety.

TECHNICAL FIELD

The present invention concerns Scleritine and its use as agent protecting cells against toxic agents.

The field of the invention concerns the pharmaceutical or cosmetic industry and more specifically the formulation of pharmaceutical or cosmetic compositions intended for protecting cells against toxic agents.

STATE OF THE TECHNIQUE

The field of cosmetics is constantly looking for new molecules with cosmetic or dermatological effects. Market demand is increasingly oriented towards natural products that are environmentally and human-friendly.

Corals are organisms whose cellular and molecular physiology is still relatively unknown and which live individually for up to several decades. They survive over long periods of time, although they are constantly exposed to bacterial, viral and fungal attacks, but also to environmental hazards due to climatic effects or pollution-related hazards; many opportunistic or specialized parasitic or predatory organisms are also a nuisance to them. The resistance of corals against all these harmful effects therefore leads to a potential source of new natural molecules with interesting effects in the cosmetic, dermatological or pharmaceutical fields.

Scleritine is a protein that was isolated and characterized for the first time in 2012 as described in Debreuil et al. "Molecular cloning and characterization of first organic matrix protein from sclerites of red coral, *Corallium rubrum* J Biol Chem. 2012 Jun. 1; 287 (23): 19367-76 Epub 2012 Apr. 13.

This protein is extracted from the organic matrix of octocoralliar sclerites, *Corallium rubrum*, more commonly known as red coral. Scleritine is the majority protein in the EDTA-soluble fraction of the organic matrix. Scleritine is a secreted phosphorylated basic protein having a sequence of 135 amino acids and a signal peptide of 20 amino acids.

ABSTRACT

The present invention proposes the use of Scleritine as a protective agent for cells against toxic agents, i.e. the invention relates to Scleritine for its use in a therapeutic treatment, advantageously dermatological, as a protective agent for cells against toxic agents.

The invention relates to Scleritine for its use in the prevention and protection of cells against toxic agents.

Surprisingly, this coral-derived protein has a protective effect for cells against toxic agents.

Advantageously, toxic agents are of different types such as chemical agents or physical agents.

From another standpoint, the invention relates to a composition, advantageously dermatological and/or cosmetic, which preferably protects the skin against toxic agents, characterized in that it comprises Scleritine in at least one excipient or vehicle adapted to a topical application.

BRIEF DESCRIPTION OF THE FIGURES AND SEQUENCES

The purposes, objects, characteristics and advantages of the invention will be best illustrated by a detailed description of a method of implementing it, illustrated by the following accompanying figures in which:

FIG. 1: schematic diagram of the general structure of the recombinant Scleritine protein. The first twenty amino acids represent the signal peptide, cleaved during the process of intracellular maturation of the protein (thus not present in the secreted mature protein). The six C-terminal histidines of the protein represent the histidine tag (HIS×6) useful for the purification process of recombinant Scleritine.

Figure 2:
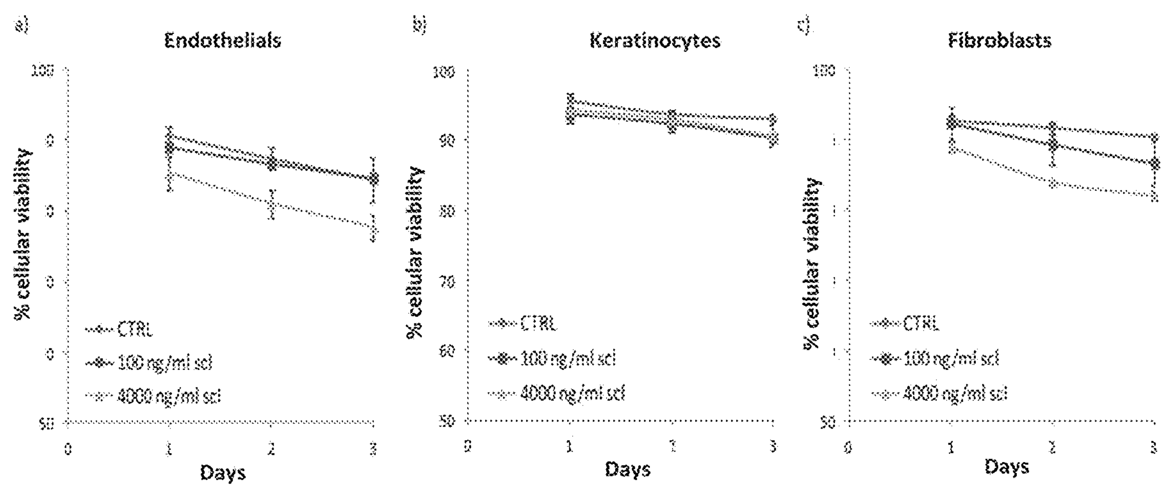

FIG. 2: graphs illustrating the viability of cell lines a) Endothelials, b) Keratinocytes, c) Fibroblasts, exposed to Scleritine in different dose rates over 3 days.

Figure 3:
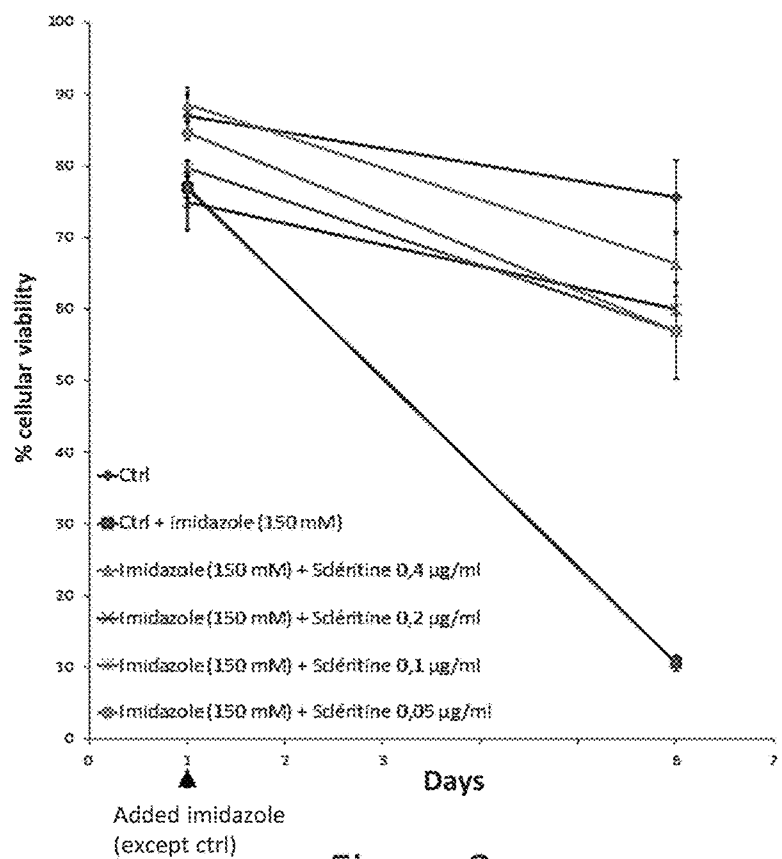

FIG. 3: graph illustrating the viability of human endothelial cells exposed to a toxic agent (imidazole at 150 mM final) in the presence of increasing doses of Scleritine over 6 days.

Figure 4:
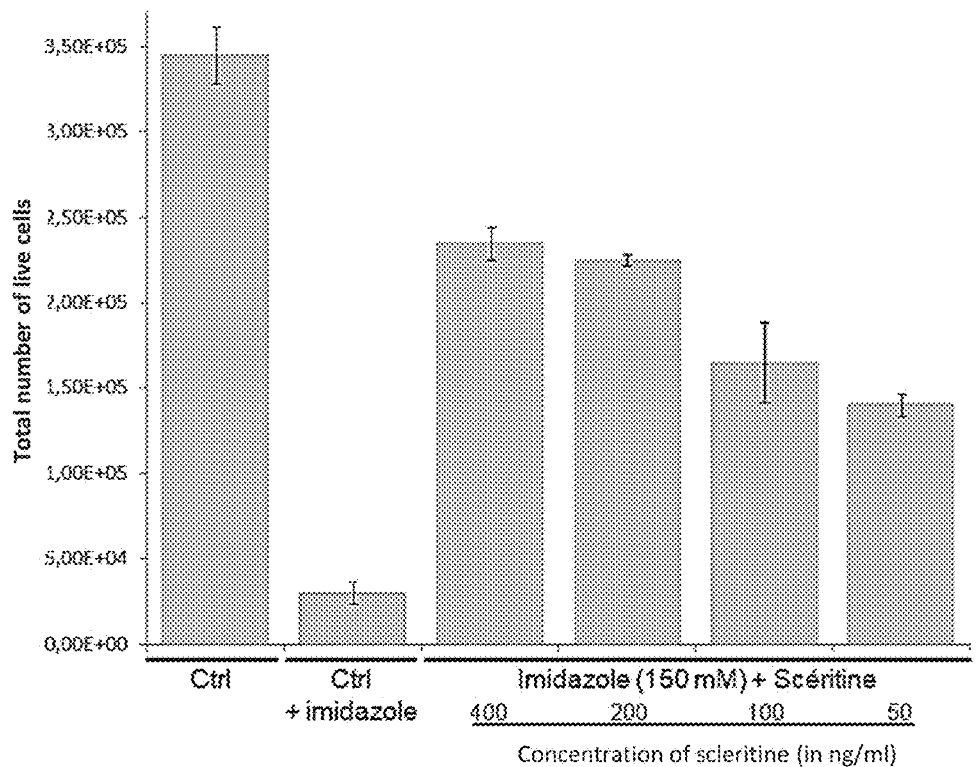

FIG. 4: graph from FIG. 3 showing the total number of live cells on Day 6 under the conditions of FIG. 3.

Figure 5:
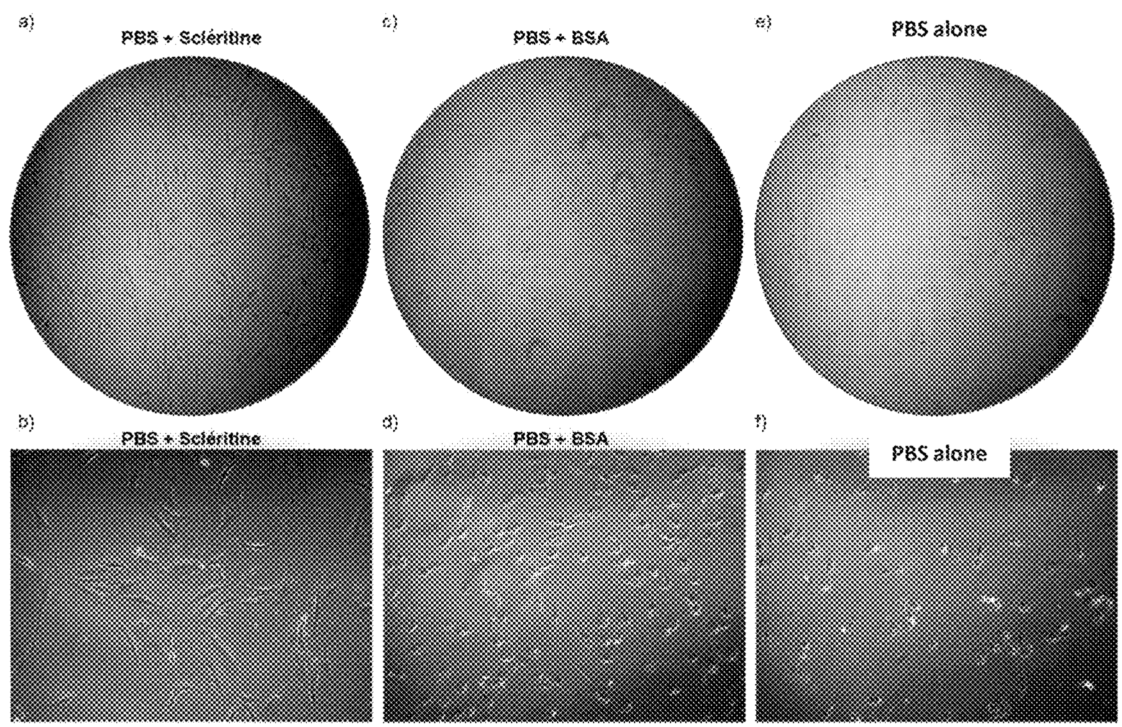

FIG. 5: Inverted phase contrast microscope images of human fibroblasts subjected to ultraviolet radiation on day 1, a) and b) in the presence of Scleritine at 4 μg/ml, c) and d) in the presence of BSA at 4 μg/ml or e) and f) in the presence of PBS alone. (80× magnification for top photos a, c and e, and 200× magnification for bottom photos b, d and f)

Figure 6:
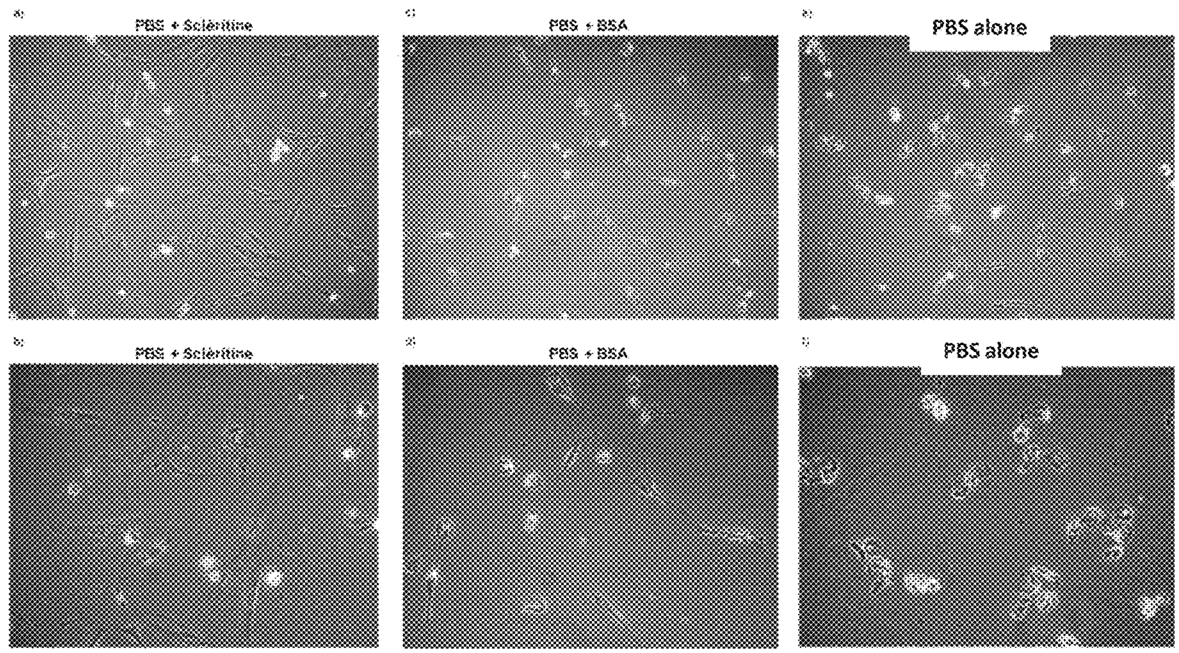

FIG. 6: Inverted phase contrast microscope images of human fibroblasts exposed to ultraviolet radiation on day 3—a) and b) in the presence of Scleritine at 4 μg/ml, c) and d) in the presence of BSA at 4 μg/ml or e) and f) in the presence of PBS alone (200× magnification for top photos a, c and e, and 400× magnification for bottom photos b, d and f)

SEQ ID NO 1: A naturally occurring nucleotide sequence of Scleritine, comprising 468 nucleotides, referenced in the NCBI GenBank catalogue as JQ652458.

SEQ ID NO 2: A codon-optimized Scleritine sequence comprising 486 nucleotides, obtained by synthesis, for improved transcriptional handling by the baculovirus/insect cell production system. In addition, it has an addition of 18 base pairs at its 3' end coding for a histidine tag. The optimized sequence, excluding the histidine tag, has an identity of 346 base pairs out of a total of 468 with the natural sequence, i.e. a nucleotide homology of 74%.

SEQ ID NO 3: 155 amino acid protein sequence of natural Scleritine.

SEQ ID NO 4: recombinant Scleritine protein sequence encoded from the optimized sequence SEQ ID NO 2. Excluding the histidine tag, it has 100% homology with the natural protein sequence.

DETAILED DESCRIPTION OF SPECIAL EMBODIMENTS

Before embarking on a detailed review of ways of implementing the invention, optional features are set out below possibly used in combination or alternatively.

First of all, we should consider the use of Scleritine as agent for protecting cells agent against toxic agents.

Advantageously, according to preferred, but not limiting variants, the invention is such that:

the toxic agents are chemical agents;

the chemical agents are selected from inorganic substances, volatile organic compounds, oxidizing agents, strong bases and acids, imidazole compounds.

chemical agents are selected from biological origin chemical agents including animal toxins and venoms.

the chemical agents are selected from among chemotherapeutic cytotoxic agents, including alkylating agents, antimetabolites, alkaloid agents, anti-cancer antibiotics.

the toxic agents are physical agents;

the physical agents are ultraviolet radiation;

Scleritine does not exhibit cytotoxicity to cells at doses less than or equal to 4000 ng/ml;

the cells are animal cells;

the cells are skin cells;

use is for the protection of the skin;

the cells are fibroblasts, endothelial cells or epithelial cells, especially keratinocytes;

use is by topical application; Scleritine is in a suitable form for topical administration;

the viability of cells exposed to a toxic agent in the presence of Scleritine is 30% greater than the viability of cells exposed to a toxic agent alone; i.e. in the absence of Scleritine, the Scleritine protein has homology of at least 90% with the protein sequence SEQ ID NO 3;

The Scleritine is in a form suitable for application to the skin prior to exposure or contact with a toxic agent.

From another standpoint, the invention relates to a composition, advantageously dermatological and/or cosmetic, which preferably protects the skin against toxic agents, characterized in that it comprises Scleritine in at least one excipient or vehicle adapted to a topical application, for instance to the skin.

One possibility is that the composition comprises an amount of Scleritin less than or equal to 4000 ng/ml of culture medium so as not to represent cytotoxicity as concerns the cells.

From another standpoint, the invention concerns a non-therapeutic method of protecting the skin against toxic agents, characterized in that it comprises applying a composition comprising Scleritine to the skin before exposure or contact with a toxic agent.

The invention concerns Scleritine which is a protein of 135 amino acids. This protein is encoded by a nucleotide sequence gene SEQ ID No. 1. The Scleritine amino acid sequence is shown opposite the nucleotide sequence in FIG. 1. Scleritine comprises a signal peptide of 20 amino acids.

According to the invention, Scleritine is produced by transfection of mammalian cells or preferably by a baculovirus/insect cell system. For example, Scleritine is produced using the process described in the publication, Buclez P O et al. "Rapid, scalable, and low-cost purification of recombinant adeno-associated virus produced by baculovirus expression vector system". Mol Ther Methods Clin Dev. 2016 May 11; 3:16035. doi: 10.1038/mtm.2016.35. For production, Scleritine may comprise a purification label also called a "tag" and for example a histidine tag comprising 6 histidines, placed after the amino acid sequence of Scleritine, as shown in FIG. 1. In addition, the Scleritine gene may have undergone the optimization of these original codons for better transcriptional handling in the internal environment of insect cells (Sf9-type producing cell lines), as illustrated by SEQ ID NO 2. This optimization can result from a difference in nucleotide sequences of up to 30% compared to the natural sequence SEQ ID NO1.

The invention extends to all the proteins comprising at least the protein sequence SEQ ID NO 3 with a homology of 90% preferably 100%.

According to the invention, Scleritine plays a protective role for the cells against toxic agents.

Advantageously, a protective agent for cells subjected to a toxic agent is understood to mean a product that allows the cells to maintain at least 60% viability at 6 days. The protective agent at least partially counteracts the harmful effects of the toxic agent. Thus, according to the invention, the difference in cell viability at day 6 is at least 30% between cells subjected to a toxic agent in the presence of Scleritine and cells subjected to a toxic agent without Scleritine.

Toxic agents are chemical agents or physical agents that are toxic to cells, i.e. they damage them, and in particular reduce the viability of cells exposed to the toxic agent.

Chemical agents include cytotoxic agents, i.e. substances that are toxic to cells, possibly to the point of destroying them.

For example, toxic agents are selected from at least one of the following:

the chemical agents among which are inorganic substances, volatile organic compounds, oxidizing agents, strong bases and acids, imidazole compounds.

chemical agents of biological origin chemical agents including animal toxins and venoms the chemotherapeutic cytotoxic agents, including alkylating agents, antimetabolites, alkaloid agents, anti-cancer antibiotics.

Physical agents include radiation, in particular ultraviolet radiation, including UVA (i.e. electromagnetic radiation at wavelengths of between 400 and 315 nm), UVB (i.e. electromagnetic radiation at wavelengths of between 315 and 280 nm) and UVC (i.e. electromagnetic radiation at wavelengths of between 280 and 100 nm).

The cells protected by Scleritine are animal eukaryotic cells, including human cells.

Preferably, Scleritine is used as a skin protective agent.

For example, animal cells include fibroblasts, epithelial cells, preferentially keratinocytes or endothelial cells.

Surprisingly, Scleritine appears not to be cytotoxic to these cells. That is, the Median Lethal Dose where $LD_{50}$ is greater than 4000 ng/ml. These quantities are particularly high doses of substances foreign to the cell. This absence of toxicity is a significant advantage meaning that Scleritine can be considered for cosmetic and/or dermatological uses.

In addition, Scleritine has a dose-dependent protective effect.

Scleritine is advantageously introduced in a composition that can be used for cosmetic and/or dermatological purposes for a preferential protection of the skin against toxic agents.

The composition is intended for topical application. Topical means that the application is local in scope. Preferably, absorption is through the skin by cutaneous or transdermal routes, or through the mucous membranes by atrial, nasal, pulmonary, vaginal/intrauterine or ocular routes.

The composition comprises at least one excipient or vehicle suitable for topical application. Depending on the desired type of preparation (ointments, creams, gels, pastes, emulsions), the final composition may comprise one or more of the following excipients: water, white petroleum jelly, paraffin (solid or liquid), macrogols (or polyethylene glycol, PEG), petroleum jelly hydrated with sorbitan sesquioleate or glycerol monostearate (with e.g. sorbic acid as a preservative), buffered ketomacrogol (with e.g. sorbic acid as a preservative), anionic hydrophilic cream (with or without glycerol), decyl oleate, carbomers (with e.g. aminomethyl propanol as stabilizer), refrcerate (white beeswax, cetyl ester waxes), vegetable oils (e.g. sesame oil), zinc oxide (ZnO), talc, and any other excipient complying favourably with the European Pharmacopoeia concerning pharmaceutical preparations.

Example 1: Exogenous Effect of Scleritine—Cytotoxicity

Various human cell lines: endothelial, keratinocytes and fibroblasts, are brought into contact with increasing doses of Scleritin: 0, 100 ng/ml and 4000 ng/ml. The results are presented on the graphs in FIG. 2.

The cells are cultured in the culture plate wells. At t=24 h the cells are brought into contact with Scleritine (formulated in a 50 mM HEPES buffer, 50 mM NaCl, pH 7.8) which is added to the complete culture medium at doses of 0, 100 or 4000 ng Scleritine per ml of culture medium.

The day Scleritine is added is considered in the examples as day 0.

Each day the cells in a well go through cell counting as per a trypsin-EDTA detachment protocol as well as automatic counting (Countess type, Life Technology). Cell viability is quantified on slide by adding Trypan blue (vital dye) to the cell suspension.

It was found that at t=3 days, the viability of cells exposed to Scleritine was similar or slightly lower than that of unexposed control cells.

In particular, for endothelial cells on day 3: 78% viability for cells exposed to 4000 ng/ml Scleritine versus 85% viability for cells exposed to 100 ng/ml Scleritine or unexposed.

For keratinocytes on day 3: 90% viability for cells exposed to 4000 ng/ml and 100 ng/ml Scleritine versus 92% viability for unexposed cells.

For fibroblasts on day 3: 82% viability for cells exposed to 4000 ng/ml, 88% viability for cells exposed to 100 ng/ml and 90% viability for unexposed cells.

To conclude, there is no identifiable cellular cytotoxicity of Scleritine on primary human cells (up to Scleritin doses of 4000 ng/ml culture medium).

Example 2: Exogenous Effect of Scleritine—Protection Against Chemical Agents

Primary human endothelial cells are brought into contact with increasing doses of Scleritin 0.4 μg/ml, 0.2 μg/ml, 0.1 μg/ml and 0.05 μg/ml and a toxic agent belonging to the family of imidazole derivatives: imidazole (CAS No. 288-32-4).

The cells are cultured in the culture plate wells. At t=24 h the cells are brought into contact with Scleritine which is added to the complete culture medium at doses of per ml of culture medium.

The day Scleritine is added is considered as day 0. 24 hours after the addition of Scleritine, the toxic agent (imidazole) is added to the culture medium for a final concentration in the medium of 150 mM. The addition of the toxic agent takes place on Day 1.

Each day the cells in a well are counted following the trypsin protocol described above.

The cells are observed through a phase contrast microscope and counted, after a trypsin protocol, every day until day 6. The results are given in the graphs of FIG. 3.

On day 6, the viability of cells exposed to imidazole alone is close to 10%, while the viability of cells exposed to imidazole in the presence of Scleritine is between 58 and 68% and the viability of control cells without imidazole and without Scleritine is 78%. These results are shown in FIG. 3.

In FIG. 4, the number of living cells on day 6 is compared under different conditions. The difference between the number of living cells with imidazole alone or in the presence of Scleritine is clearly visible.

Scleritine therefore plays a protective role for the cells against imidazole.

Example 3: Exogenous Effect of Scleritine—Protection Against Physical Agents

Human primary fibroblasts are exposed to ultraviolet radiation in the presence or absence of Scleritine.

The cells are cultured in the culture plate wells. At t=24 h, the culture medium is removed and replaced by PBS 1× (to avoid potential UV attenuation effects of soluble serum proteins). The cells are brought into contact with Scleritine in PBS 1× at a final concentration of 4 μg/ml. The cells are incubated for 30 minutes at 37° C. They are then irradiated with UltraViolet C at 254 nm at a power of 1000 $\mu J/cm^2$. 5 minutes after irradiation, complete culture medium is added to the wells and the cells are cultured in an incubator at 37° C. and 5% $CO_2$.

The day Scleritine is added is considered as day 0. UVC irradiation also takes place on day 0.

The cells in a well are controlled at J1 and J3.

FIG. 5 shows inverted phase contrast microscope images (80× magnification for FIGS. 5*a, c* and *e*, and 200× magnification for FIGS. 5*b, d* and *f*) of fibroblast plaque on day 1 after irradiation in the presence of 4 μg/ml Scleritine: FIGS. 5 *a*) and *b*), BSA at 4 μg/ml: FIGS. 5 *c*) and *d*) or PBS alone: FIGS. 5 *e*) and *f*).

The fibroblasts are found to be damaged with PBS alone or supplemented with BSA while their appearance remains correct for fibroblasts in the presence of Scleritine.

FIG. 6 shows inverted phase contrast microscope images (200× magnification for FIGS. 6*a, c* and *e*, and 400× magnification for FIGS. 6*b, d* and *f*) of fibroblast plaques on day 3 after irradiation in the presence of 4 μg/ml Scleritin: FIGS. 6 *a*) and *b*), BSA at 4 μg/ml: FIGS. 6 *c*) and *d*) or PBS alone: FIGS. 6 *e*) and *f*).

On day 1, fibroblasts irradiated in the presence of Scleritine show a typical fibroblast appearance, i.e. fusiform or star-shaped with very fine extensions. With the BSA alone, the fibroblasts are condensed, the extensions are reduced or even absent. Similarly with PBS alone, fibroblasts are condensed and extensions are reduced. From day 1, fibroblasts irradiated in the presence of PBS alone or BSA alone show an appearance typical of apoptotic bodies (programmed cell death). At this stage, attempts to quantify the concentrations of living cells in conditions with BSA or PBS alone fail due to the absence of countable cells, probably highly compromised by the irradiation protocol. The fibroblasts are found to be damaged with PBS alone or BSA alone while their appearance remains correct for fibroblasts in the presence of Scleritine.

On day 3, the observations are the same or even more emphatic: fibroblasts irradiated in the presence of Scleritine show a typical fibroblast appearance, i.e. fusiform or star-shaped with very fine extensions. With the BSA alone, the fibroblasts are condensed, and the extensions are reduced or even absent. Similarly with PBS alone, the fibroblasts are condensed and there are no extensions. The fibroblasts irradiated in the presence of PBS alone or BSA alone show an appearance typical of apoptotic bodies. At this stage, attempts to quantify the concentrations of living cells in conditions with BSA or PBS alone fail due to the absence of countable cells, probably highly compromised by the irradiation protocol.

Scleritine therefore plays a protective role for the cells against ultraviolet C rays. Ultraviolet C rays are short wavelength radiation and are therefore extremely energetic. This energy gives them considerable power to alter biological molecules. The strong protective effect of Scleritine against UVC radiation suggests that the effect of Scleritine against the less energetic UVB and UVA radiation would also be of interest.

The invention claimed is:

1. A method of using scleritine in a dermatological treatment as a protective agent for protecting cells against damage from a toxic agent, the method comprising:

applying a dermatological medicant comprising scleritine to the cells, wherein the dermatological medicant comprises a scleritine concentration not greater than 4000 ng/ml.

2. The method according to claim 1 wherein the toxic agent is a chemical agent.

3. The method according to claim 2 wherein the chemical agent is selected from the group consisting of inorganic substances, volatile organic compounds, oxidizing agents, strong bases, strong acids, and imidazole compounds.

4. The method according to claim 2 wherein the chemical agent is selected from the group consisting of chemical agents of biological origin.

5. The method according to claim 2 wherein the chemical agent is selected from the group consisting of chemotherapeutic cytotoxic agents.

6. The method according to claim 1 wherein the toxic agent is a physical agent.

7. The method according to claim 6 wherein the physical agent is ultraviolet radiation.

8. The method according to claim 7 wherein the dermatological treatment further comprises applying the dermatological medicant to human skin.

9. The method according to claim 1 wherein the cells are selected from the group consisting of fibroblasts, endothelial cells, epithelial cells, and mixtures thereof.

10. The method according to claim 1 wherein the dermatological medicant is formulated to be suitable for topical administration.

11. The method according to claim 1 wherein the scleritine has a homology of at least 90% with the protein sequence of SEQ ID NO. 3.

12. The method according to claim 10 wherein the dermatological medicant further comprises an excipient suitable for application to human skin prior to exposure to the toxic agent.

13. The method according to claim 10, wherein the dermatological medicant further comprises an excipient selected from the group consisting of coloring agents, preservatives, fillers, and mixtures thereof.

14. The method according to claim 12, further comprising: applying the dermatological medicant to a skin surface in anticipation of exposure of the skin surface to the toxic agent, wherein the dermatological medicant comprises an effective amount of scleritine.

* * * * *

SEQUENCE LISTING

```
<160> NUMBER OF SEQ ID NOS: 4

<210> SEQ ID NO 1
<211> LENGTH: 468
<212> TYPE: DNA
<213> ORGANISM: Corallium rubrum

<400> SEQUENCE: 1

atgaaatttt ttggtgcgat tttggtttgt ctacttcttg ccattccgta tggctcgcca      60

cagcagcaaa ctgtagttat gaaacacggg tttattcggc acaggaaggt tggtcagggc     120

gtaattaatc cattaagctc tgaagcagtg gcattgtttt tcaacaaaaa gtggaatact     180

tttattgaac ttagcaaacg tatgcaacga gagtcatcca atttttgcag agcgaacttc     240

ggagtcctta acgactggca aaaaagacag tgcagttgca tcagcatctt cagcttcatg     300

aaccaaggaa gggatgcaat gctggtggcg agaacaactt ttggagaaat ttggcagaat     360

tttaacaaat ttgggccaac tgaatactgc aacacacggc ctgtacagcc tatttccagg     420

cagctagatg atctttgtta ctgtatgaca ggaaatccct ctgtttga                  468


<210> SEQ ID NO 2
<211> LENGTH: 486
<212> TYPE: DNA
<213> ORGANISM: Artificial Sequence
<220> FEATURE:
<223> OTHER INFORMATION: Synthesized

<400> SEQUENCE: 2

atgaagttct tcggtgctat cctcgtgtgc ctcctgctgg ctatccccta cggctccccg      60

caacaacaga cggtcgtgat gaaacatggt ttcatccgcc accgtaaagt gggtcagggc     120

gtcattaacc cactgtccag cgaggctgtc gccctcttct tcaacaagaa atggaacact     180

ttcatcgagt tgtctaagag gatgcaaaga gaatcttcaa acttctgccg cgctaacttc     240

ggcgttctga acgactggca gaaacgccaa tgcagttgta tctcgatttt ctccttcatg     300

aaccagggac gcgatgcaat gctcgttgct cgtaccactt tcggagagat ctggcaaaac     360

ttcaacaaat tcggtccgac agaatactgt aacacgaggc ctgtgcagcc catttccaga     420

caactggacg acttgtgcta ctgtatgact ggaaacccat ccgttcacca ccaccaccat     480

cactga                                                                486


<210> SEQ ID NO 3
<211> LENGTH: 155
<212> TYPE: PRT
<213> ORGANISM: Corallium rubrum

<400> SEQUENCE: 3

Met Lys Phe Phe Gly Ala Ile Leu Val Cys Leu Leu Leu Ala Ile Pro
1               5                   10                  15
```

```
Tyr Gly Ser Pro Gln Gln Gln Thr Val Val Met Lys His Gly Phe Ile
            20                  25                  30

Arg His Arg Lys Val Gly Gln Gly Val Ile Asn Pro Leu Ser Ser Glu
        35                  40                  45

Ala Val Ala Leu Phe Phe Asn Lys Lys Trp Asn Thr Phe Ile Glu Leu
    50                  55                  60

Ser Lys Arg Met Gln Arg Glu Ser Ser Asn Phe Cys Arg Ala Asn Phe
65                  70                  75                  80

Gly Val Leu Asn Asp Trp Gln Lys Arg Gln Cys Ser Cys Ile Ser Ile
                85                  90                  95

Phe Ser Phe Met Asn Gln Gly Arg Asp Ala Met Leu Val Ala Arg Thr
            100                 105                 110

Thr Phe Gly Glu Ile Trp Gln Asn Phe Asn Lys Phe Gly Pro Thr Glu
        115                 120                 125

Tyr Cys Asn Thr Arg Pro Val Gln Pro Ile Ser Arg Gln Leu Asp Asp
    130                 135                 140

Leu Cys Tyr Cys Met Thr Gly Asn Pro Ser Val
145                 150                 155


<210> SEQ ID NO 4
<211> LENGTH: 161
<212> TYPE: PRT
<213> ORGANISM: Artificial Sequence
<220> FEATURE:
<223> OTHER INFORMATION: Synthesized

<400> SEQUENCE: 4

Met Lys Phe Phe Gly Ala Ile Leu Val Cys Leu Leu Leu Ala Ile Pro
1               5                   10                  15

Tyr Gly Ser Pro Gln Gln Gln Thr Val Val Met Lys His Gly Phe Ile
            20                  25                  30

Arg His Arg Lys Val Gly Gln Gly Val Ile Asn Pro Leu Ser Ser Glu
        35                  40                  45

Ala Val Ala Leu Phe Phe Asn Lys Lys Trp Asn Thr Phe Ile Glu Leu
    50                  55                  60

Ser Lys Arg Met Gln Arg Glu Ser Ser Asn Phe Cys Arg Ala Asn Phe
65                  70                  75                  80

Gly Val Leu Asn Asp Trp Gln Lys Arg Gln Cys Ser Cys Ile Ser Ile
                85                  90                  95

Phe Ser Phe Met Asn Gln Gly Arg Asp Ala Met Leu Val Ala Arg Thr
            100                 105                 110

Thr Phe Gly Glu Ile Trp Gln Asn Phe Asn Lys Phe Gly Pro Thr Glu
        115                 120                 125

Tyr Cys Asn Thr Arg Pro Val Gln Pro Ile Ser Arg Gln Leu Asp Asp
    130                 135                 140

Leu Cys Tyr Cys Met Thr Gly Asn Pro Ser Val His His His His His
145                 150                 155                 160

His
```